(12) United States Patent
Vargas et al.

(10) Patent No.: US 7,309,343 B2
(45) Date of Patent: *Dec. 18, 2007

(54) METHOD FOR CUTTING TISSUE

(75) Inventors: Jaime Vargas, Palo Alto, CA (US);
Brendan M. Donohoe, San Francisco, CA (US); Scott C. Anderson, Sunnyvale, CA (US); Theodore Bender, Palo Alto, CA (US); Stephen Yencho, Menlo Park, CA (US); Bernard Hausen, Menlo Park, CA (US); Michael Hendricksen, Menlo Park, CA (US); James T. Nielsen, San Francisco, CA (US)

(73) Assignee: Cardica, Inc., Redwood City, CA (US)

( * ) Notice: Subject to any disclaimer, the term of this patent is extended or adjusted under 35 U.S.C. 154(b) by 453 days.

This patent is subject to a terminal disclaimer.

(21) Appl. No.: 10/698,575

(22) Filed: Oct. 31, 2003

(65) Prior Publication Data
US 2004/0098011 A1    May 20, 2004

Related U.S. Application Data

(63) Continuation of application No. 09/542,976, filed on Apr. 4, 2000, now Pat. No. 6,673,088, which is a continuation-in-part of application No. 09/440,263, filed on Nov. 15, 1999, now Pat. No. 6,371,964, which is a continuation-in-part of application No. 09/314,278, filed on May 18, 1999, now Pat. No. 6,428,550.

(51) Int. Cl.
*A61B 17/34* (2006.01)

(52) U.S. Cl. .................................................... 606/185
(58) Field of Classification Search ............... 606/184, 606/185, 170, 174, 180, 187, 159, 171, 167; 604/22, 164, 264
See application file for complete search history.

(56) References Cited

U.S. PATENT DOCUMENTS 2,370,776 A    3/1945   Carlson (Continued)

FOREIGN PATENT DOCUMENTS

DE    29713336    11/1997

(Continued)

OTHER PUBLICATIONS

"Cardica PAS-Port Proximal Anastomosis System 510(k)", Section VI.C., "Substantial Equivalence", and Attachment 7 (Unpublished).

(Continued)

*Primary Examiner*—Kevin T. Truong
(74) *Attorney, Agent, or Firm*—Brian A. Schar

(57) ABSTRACT

A tissue punch for creating a hole in the wall of a target blood vessel for receiving an anastomosis device includes a piercing element for penetrating the tissue and a cutting element for cutting a plug of tissue around the pierced hole. The tissue punch includes a trocar for inserting the piercing element. After punching is complete, the piercing element is removed from the trocar through a side wall of the trocar so that a medical device can be deployed through the trocar lumen. The tissue punch may also include a tissue trap for trapping the plug of tissue.

15 Claims, 11 Drawing Sheets

U.S. PATENT DOCUMENTS

| | | |
|---|---|---|
| 3,254,650 A | 6/1966 | Collito |
| 3,254,651 A | 6/1966 | Collito |
| 3,519,187 A | 7/1970 | Kapitanov et al. |
| 3,774,615 A | 11/1973 | Lim et al. |
| 3,777,538 A | 12/1973 | Weatherly et al. |
| 3,995,619 A | 12/1976 | Glatzer |
| 4,018,228 A | 4/1977 | Goosen |
| 4,118,806 A | 10/1978 | Porier et al. |
| 4,214,587 A | 7/1980 | Sakura, Jr. |
| 4,217,664 A | 8/1980 | Faso |
| 4,350,160 A | 9/1982 | Kolesov et al. |
| 4,352,358 A | 10/1982 | Angelchik |
| 4,366,819 A | 1/1983 | Kaster |
| 4,368,736 A | 1/1983 | Kaster |
| 4,503,568 A | 3/1985 | Madras |
| 4,523,529 A | 6/1985 | Poll |
| 4,534,761 A | 8/1985 | Raible |
| 4,553,542 A | 11/1985 | Schenck et al. |
| 4,577,631 A | 3/1986 | Kreamer |
| 4,589,416 A | 5/1986 | Green |
| 4,593,693 A | 6/1986 | Schenck |
| 4,603,693 A | 8/1986 | Conta et al. |
| 4,607,637 A | 8/1986 | Berggren et al. |
| 4,624,255 A | 11/1986 | Schenck et al. |
| 4,624,257 A | 11/1986 | Berggren et al. |
| 4,625,727 A | 12/1986 | Leiboff |
| 4,628,550 A | 12/1986 | Walton |
| 4,657,019 A | 4/1987 | Walsh et al. |
| 4,665,906 A | 5/1987 | Jervis |
| 4,721,109 A | 1/1988 | Healey |
| 4,747,407 A | 5/1988 | Liu et al. |
| 4,752,024 A | 6/1988 | Green et al. |
| 4,773,420 A | 9/1988 | Green |
| 4,861,330 A | 8/1989 | Voss |
| 4,875,815 A | 10/1989 | Phillips, II |
| 4,883,453 A | 11/1989 | Berry et al. |
| 4,892,098 A | 1/1990 | Sauer |
| 4,907,591 A | 3/1990 | Vasconcellos et al. |
| 4,917,087 A | 4/1990 | Walsh et al. |
| 4,917,090 A | 4/1990 | Berggren et al. |
| 4,917,091 A | 4/1990 | Berggren et al. |
| 4,930,674 A | 6/1990 | Barak |
| 5,005,749 A | 4/1991 | Aranyi |
| 5,015,238 A | 5/1991 | Solomon et al. |
| 5,062,842 A | 11/1991 | Tiffany |
| 5,089,006 A | 2/1992 | Stiles |
| 5,100,423 A | 3/1992 | Fearnot |
| 5,104,025 A | 4/1992 | Main et al. |
| 5,119,983 A | 6/1992 | Green et al. |
| 5,129,913 A | 7/1992 | Ruppert |
| 5,156,613 A | 10/1992 | Sawyer |
| 5,156,619 A | 10/1992 | Ehrenfeld |
| 5,171,262 A | 12/1992 | MacGregor |
| 5,178,634 A | 1/1993 | Ramos Martinez |
| 5,187,796 A | 2/1993 | Wang et al. |
| 5,192,289 A | 3/1993 | Jessen |
| 5,192,294 A * | 3/1993 | Blake, III .................. 606/184 |
| 5,193,731 A | 3/1993 | Aranyi |
| 5,199,983 A | 4/1993 | Katamoto |
| 5,205,459 A | 4/1993 | Brinkerhoff et al. |
| 5,211,683 A | 5/1993 | Maginot |
| 5,217,474 A | 6/1993 | Zacca et al. |
| 5,221,259 A | 6/1993 | Weldon et al. |
| 5,221,281 A | 6/1993 | Klicek |
| 5,221,683 A | 6/1993 | Ulrich et al. |
| 5,222,963 A | 6/1993 | Brinkerhoff et al. |
| 5,234,447 A | 8/1993 | Kaster et al. |
| 5,250,058 A | 10/1993 | Miller et al. |
| 5,250,060 A | 10/1993 | Carbo et al. |
| 5,271,544 A | 12/1993 | Fox et al. |
| 5,275,322 A | 1/1994 | Brinkerhoff et al. |
| 5,285,945 A | 2/1994 | Brinkerhoff et al. |
| 5,290,298 A | 3/1994 | Rebuffat et al. |
| 5,292,053 A | 3/1994 | Bilotti et al. |
| 5,304,220 A | 4/1994 | Maginot |
| 5,314,435 A | 5/1994 | Green et al. |
| 5,314,468 A | 5/1994 | Martinez |
| 5,326,205 A | 7/1994 | Anspach, Jr. et al. |
| 5,333,773 A | 8/1994 | Main et al. |
| 5,336,233 A | 8/1994 | Chen |
| 5,350,104 A | 9/1994 | Main et al. |
| 5,354,302 A | 10/1994 | Ko |
| 5,364,389 A | 11/1994 | Anderson |
| 5,366,462 A | 11/1994 | Kaster et al. |
| 5,392,979 A | 2/1995 | Green et al. |
| 5,395,030 A | 3/1995 | Kuramoto et al. |
| 5,395,311 A | 3/1995 | Andrews |
| 5,401,131 A | 3/1995 | Yoshino |
| 5,403,338 A | 4/1995 | Milo |
| 5,443,497 A | 8/1995 | Venbrux |
| 5,447,514 A | 9/1995 | Gerry et al. |
| 5,454,825 A | 10/1995 | Van Leeuwen |
| 5,456,712 A | 10/1995 | Maginot |
| 5,456,714 A | 10/1995 | Owen |
| 5,464,449 A | 11/1995 | Ryan et al. |
| 5,465,895 A | 11/1995 | Knodel et al. |
| 5,470,320 A | 11/1995 | Tiefenbrun et al. |
| 5,478,354 A | 12/1995 | Tovey |
| 5,503,635 A | 4/1996 | Sauer et al. |
| 5,515,478 A | 5/1996 | Wang |
| 5,522,834 A | 6/1996 | Fonger et al. |
| 5,524,180 A | 6/1996 | Wang et al. |
| 5,533,661 A | 7/1996 | Main et al. |
| 5,540,677 A | 7/1996 | Sinofsky |
| 5,553,198 A | 9/1996 | Wang et al. |
| 5,556,405 A | 9/1996 | Lary |
| 5,558,667 A | 9/1996 | Yarborough et al. |
| 5,571,167 A | 11/1996 | Maginot |
| 5,603,721 A | 2/1997 | Lau et al. |
| 5,643,340 A | 7/1997 | Nunokawa |
| 5,645,520 A | 7/1997 | Nakamura et al. |
| 5,657,429 A | 8/1997 | Wang et al. |
| 5,667,513 A | 9/1997 | Torrie et al. |
| 5,667,520 A | 9/1997 | Bonutti |
| 5,669,918 A | 9/1997 | Balazs et al. |
| 5,669,934 A | 9/1997 | Sawyer |
| 5,676,670 A | 10/1997 | Kim |
| 5,693,088 A | 12/1997 | Lazarus |
| 5,695,504 A | 12/1997 | Gifford, III et al. |
| 5,702,412 A | 12/1997 | Popov et al. |
| 5,707,362 A | 1/1998 | Yoon |
| 5,707,380 A | 1/1998 | Hinchliffe et al. |
| 5,709,335 A | 1/1998 | Heck |
| 5,709,693 A | 1/1998 | Taylor |
| 5,720,756 A | 2/1998 | Green et al. |
| 5,725,544 A | 3/1998 | Rygaard |
| 5,725,553 A | 3/1998 | Moenning |
| 5,732,872 A | 3/1998 | Bolduc et al. |
| 5,754,741 A | 5/1998 | Wang et al. |
| 5,755,778 A | 5/1998 | Kleshinski |
| 5,762,458 A | 6/1998 | Wang et al. |
| 5,779,718 A | 7/1998 | Green et al. |
| 5,782,397 A | 7/1998 | Koukline |
| 5,792,135 A | 8/1998 | Madhani et al. |
| 5,797,900 A | 8/1998 | Madhani et al. |
| 5,797,920 A | 8/1998 | Kim |
| 5,799,661 A | 9/1998 | Boyd et al. |
| 5,799,857 A | 9/1998 | Robertson et al. |
| 5,807,377 A | 9/1998 | Madhani et al. |
| 5,814,073 A | 9/1998 | Bonutti |
| 5,815,640 A | 9/1998 | Wang et al. |
| 5,817,113 A | 10/1998 | Gifford, III et al. |
| 5,827,316 A | 10/1998 | Young et al. |
| 5,833,698 A | 11/1998 | Hinchliffe et al. |

| | | |
|---|---|---|
| 5,841,950 A | 11/1998 | Wang et al. |
| 5,855,583 A | 1/1999 | Wang et al. |
| 5,868,761 A | 2/1999 | Nicholas et al. |
| 5,868,763 A | 2/1999 | Spence et al. |
| 5,871,495 A | 2/1999 | Mueller |
| 5,875,782 A | 3/1999 | Ferrari et al. |
| 5,878,193 A | 3/1999 | Wang et al. |
| 5,879,371 A | 3/1999 | Gardiner et al. |
| 5,881,943 A | 3/1999 | Heck et al. |
| 5,893,369 A | 4/1999 | LeMole |
| 5,904,697 A | 5/1999 | Gifford, III et al. |
| 5,907,664 A | 5/1999 | Wang et al. |
| 5,910,153 A * | 6/1999 | Mayenberger ............... 606/184 |
| 5,911,036 A | 6/1999 | Wright et al. |
| 5,915,616 A | 6/1999 | Viola et al. |
| 5,921,957 A | 7/1999 | Killion et al. |
| 5,921,995 A | 7/1999 | Kleshinski |
| 5,931,842 A | 8/1999 | Goldsteen et al. |
| 5,944,730 A | 8/1999 | Nobles et al. |
| 5,947,363 A | 9/1999 | Bolduc et al. |
| 5,957,363 A | 9/1999 | Heck |
| 5,968,089 A | 10/1999 | Krajicek |
| 5,972,014 A | 10/1999 | Nevins |
| 5,976,159 A | 11/1999 | Bolduc et al. |
| 5,976,178 A | 11/1999 | Goldsteen et al. |
| 5,979,920 A | 11/1999 | Krakowiak et al. |
| 5,989,278 A | 11/1999 | Mueller |
| 6,001,124 A | 12/1999 | Bachinski |
| 6,007,544 A | 12/1999 | Kim |
| 6,013,190 A | 1/2000 | Berg et al. |
| 6,015,416 A | 1/2000 | Stefanchik et al. |
| 6,022,367 A | 2/2000 | Sherts |
| 6,030,370 A | 2/2000 | Kupka et al. |
| 6,030,395 A | 2/2000 | Nash et al. |
| 6,036,699 A | 3/2000 | Andreas et al. |
| 6,036,700 A | 3/2000 | Stefanchik et al. |
| 6,036,702 A | 3/2000 | Bachinkski et al. |
| 6,036,703 A | 3/2000 | Evans et al. |
| 6,036,704 A | 3/2000 | Yoon |
| 6,036,705 A | 3/2000 | Nash et al. |
| 6,050,472 A | 4/2000 | Shibata |
| 6,053,390 A | 4/2000 | Green et al. |
| 6,056,762 A | 5/2000 | Nash et al. |
| 6,066,144 A | 5/2000 | Wolf et al. |
| 6,066,148 A | 5/2000 | Rygaard |
| 6,068,637 A | 5/2000 | Popov et al. |
| 6,074,416 A | 6/2000 | Berg et al. |
| 6,080,167 A | 6/2000 | Lyell |
| 6,080,173 A | 6/2000 | Williamson, IV et al. |
| 6,083,234 A | 7/2000 | Nicholas et al. |
| 6,110,188 A | 8/2000 | Narciso, Jr. |
| 6,113,612 A | 9/2000 | Swanson et al. |
| 6,117,148 A | 9/2000 | Ravo et al. |
| 6,120,432 A | 9/2000 | Sullivan et al. |
| 6,132,439 A | 10/2000 | Kontos |
| 6,136,014 A | 10/2000 | Sirimanne et al. |
| 6,146,393 A | 11/2000 | Wakabayashi |
| 6,149,681 A | 11/2000 | Houser et al. |
| 6,152,937 A | 11/2000 | Peterson et al. |
| 6,152,945 A | 11/2000 | Bachinski et al. |
| 6,165,185 A | 12/2000 | Shennib et al. |
| 6,167,889 B1 | 1/2001 | Benetti |
| 6,171,319 B1 | 1/2001 | Nobles et al. |
| 6,171,321 B1 | 1/2001 | Gifford, III et al. |
| 6,176,413 B1 | 1/2001 | Heck et al. |
| 6,176,864 B1 | 1/2001 | Chapman |
| 6,179,848 B1 | 1/2001 | Solem |
| 6,186,942 B1 | 2/2001 | Sullivan et al. |
| 6,187,019 B1 | 2/2001 | Stefanchik et al. |
| 6,187,020 B1 | 2/2001 | Zegdi et al. |
| 6,190,396 B1 | 2/2001 | Whitin et al. |
| 6,190,397 B1 | 2/2001 | Spence et al. |
| 6,190,590 B1 | 2/2001 | Randall et al. |
| 6,193,129 B1 | 2/2001 | Bittner et al. |
| 6,193,734 B1 | 2/2001 | Bolduc et al. |
| 6,206,912 B1 | 3/2001 | Goldsteen et al. |
| 6,206,913 B1 | 3/2001 | Yencho et al. |
| 6,235,054 B1 | 5/2001 | Berg et al. |
| 6,254,651 B1 | 7/2001 | Brooke et al. |
| 6,302,905 B1 | 10/2001 | Goldsteen et al. |
| 6,309,416 B1 | 10/2001 | Swanson et al. |
| 6,371,964 B1 | 4/2002 | Vargas et al. |
| 6,391,036 B1 | 5/2002 | Berg et al. |
| 6,402,764 B1 | 6/2002 | Hendricksen |
| 6,428,550 B1 | 8/2002 | Vargas et al. |
| 6,451,048 B1 | 9/2002 | Berg et al. |
| 6,461,320 B1 | 10/2002 | Yencho et al. |
| 6,485,496 B1 | 11/2002 | Suyker et al. |
| 6,524,322 B1 | 2/2003 | Berreklouw |
| 6,605,098 B2 | 8/2003 | Nobis et al. |
| 6,673,088 B1 | 1/2004 | Vargas et al. |
| 6,695,859 B1 | 2/2004 | Golden et al. |
| 6,699,256 B1 * | 3/2004 | Logan et al. ............... 606/153 |
| 6,966,917 B1 | 11/2005 | Suyker et al. |
| 2001/0047180 A1 | 11/2001 | Grudem et al. |
| 2002/0058955 A1 | 5/2002 | Blatter et al. |
| 2002/0082614 A1 | 6/2002 | Logan et al. |
| 2003/0065342 A1 | 4/2003 | Nobis |

FOREIGN PATENT DOCUMENTS

| | | |
|---|---|---|
| EP | 0 517 252 | 12/1992 |
| EP | 0 701 800 | 3/1996 |
| EP | 0 885 595 | 12/1998 |
| EP | 0 938 870 | 9/1999 |
| EP | 0 820 724 | 1/2000 |
| EP | 0 820 725 | 1/2000 |
| EP | 0 913 125 | 7/2000 |
| EP | 0 990 420 | 12/2000 |
| FR | 2316910 | 4/1977 |
| WO | 92/08513 | 5/1992 |
| WO | 96/25886 | 8/1996 |
| WO | 97/25002 | 7/1997 |
| WO | 97/27898 | 8/1997 |
| WO | 97/31575 | 9/1997 |
| WO | 98/07399 | 2/1998 |
| WO | 98/19608 | 5/1998 |
| WO | 98/19618 | 5/1998 |
| WO | 98/19625 | 5/1998 |
| WO | 98/19629 | 5/1998 |
| WO | 98/19630 | 5/1998 |
| WO | 98/19631 | 5/1998 |
| WO | 98/19632 | 5/1998 |
| WO | 98/19634 | 5/1998 |
| WO | 98/19636 | 5/1998 |
| WO | 98/30153 | 7/1998 |
| WO | 98/37814 | 9/1998 |
| WO | 98/40036 | 9/1998 |
| WO | 98/42262 | 10/1998 |
| WO | 98/47430 | 10/1998 |
| WO | 98/55027 | 12/1998 |
| WO | 99/08603 | 2/1999 |
| WO | 99/11178 | 3/1999 |
| WO | 99/17665 | 4/1999 |
| WO | 99/18887 | 4/1999 |
| WO | 99/21491 | 5/1999 |
| WO | 99/37218 | 7/1999 |
| WO | 99/38441 | 8/1999 |
| WO | 99/38454 | 8/1999 |
| WO | 99/40851 | 8/1999 |
| WO | 99/40868 | 8/1999 |
| WO | 99/45848 | 9/1999 |
| WO | 99/52481 | 10/1999 |
| WO | 99/62406 | 12/1999 |
| WO | 99/62409 | 12/1999 |
| WO | 99/62415 | 12/1999 |

| | | |
|---|---|---|
| WO | 99/63910 | 12/1999 |
| WO | 99/985409 | 12/1999 |
| WO | 00/09040 | 2/2000 |
| WO | 00/10486 | 3/2000 |
| WO | 00/12013 | 3/2000 |
| WO | 00/15144 | 3/2000 |
| WO | 00/15146 | 3/2000 |
| WO | 00/15147 | 3/2000 |
| WO | 00/15148 | 3/2000 |
| WO | 00/15149 | 3/2000 |
| WO | 00/27310 | 5/2000 |
| WO | 00/27311 | 5/2000 |
| WO | 00/27312 | 5/2000 |
| WO | 00/27313 | 5/2000 |
| WO | 00/33745 | 6/2000 |
| WO | 00/41633 | 7/2000 |
| WO | 00/53104 | 9/2000 |
| WO | 00/56223 | 9/2000 |
| WO | 00/56227 | 9/2000 |
| WO | 00/56228 | 9/2000 |
| WO | 00/50380 | 10/2000 |
| WO | 00/66007 | 11/2000 |
| WO | 00/66009 | 11/2000 |
| WO | 00/69343 | 11/2000 |
| WO | 00/69346 | 11/2000 |
| WO | 00/69349 | 11/2000 |
| WO | 00/69364 | 11/2000 |
| WO | 00/72764 | 12/2000 |
| WO | 00/74579 | 12/2000 |
| WO | 00/76405 | 12/2000 |
| WO | 01/08601 | 2/2001 |
| WO | 01/12074 | 2/2001 |
| WO | 01/15607 | 3/2001 |
| WO | 01/17440 | 3/2001 |
| WO | 01/19257 | 3/2001 |
| WO | 01/19259 | 3/2001 |
| WO | 01/19284 | 3/2001 |
| WO | 01/34037 | 5/2001 |

OTHER PUBLICATIONS

Sales training brochure entitled "CorLink Automated Anastomosis Device" (2002).

* cited by examiner

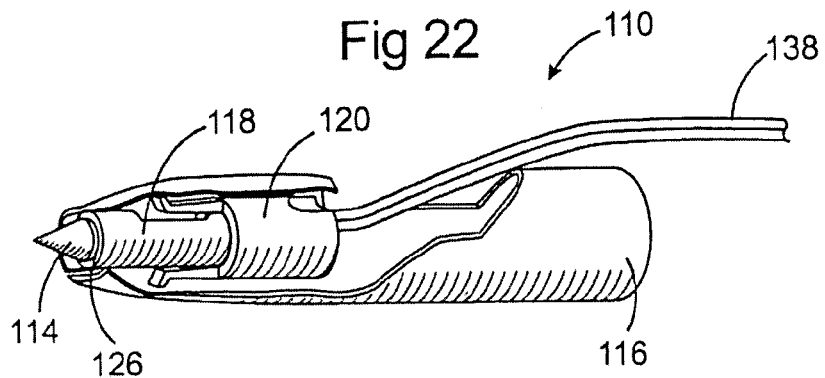
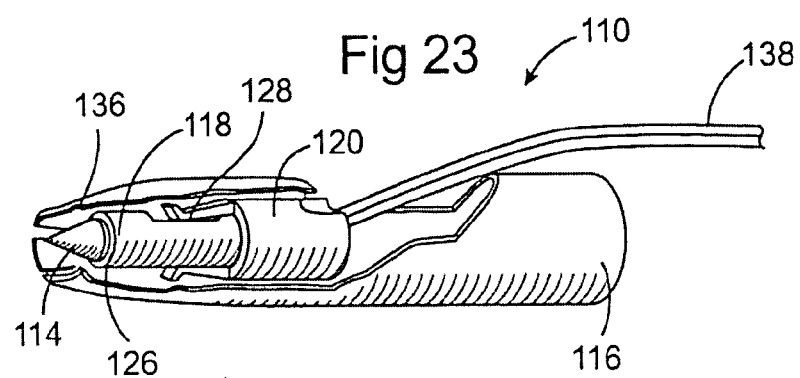
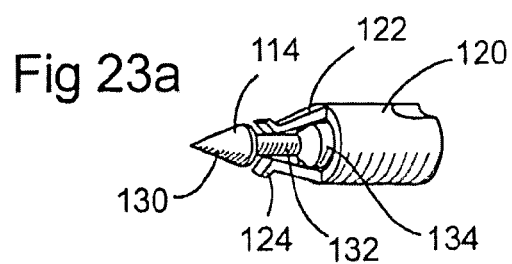
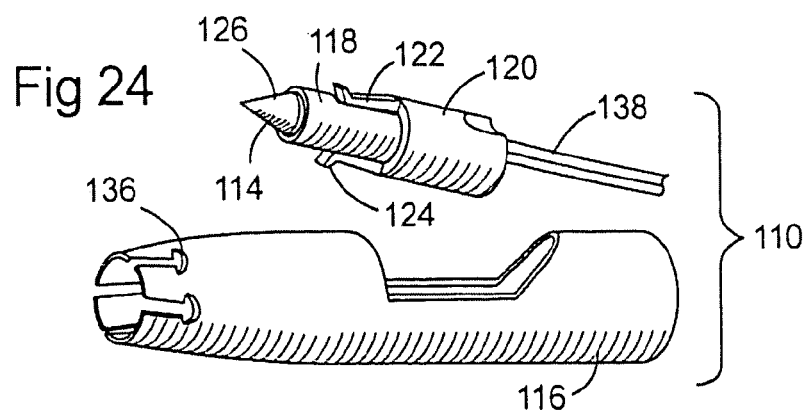

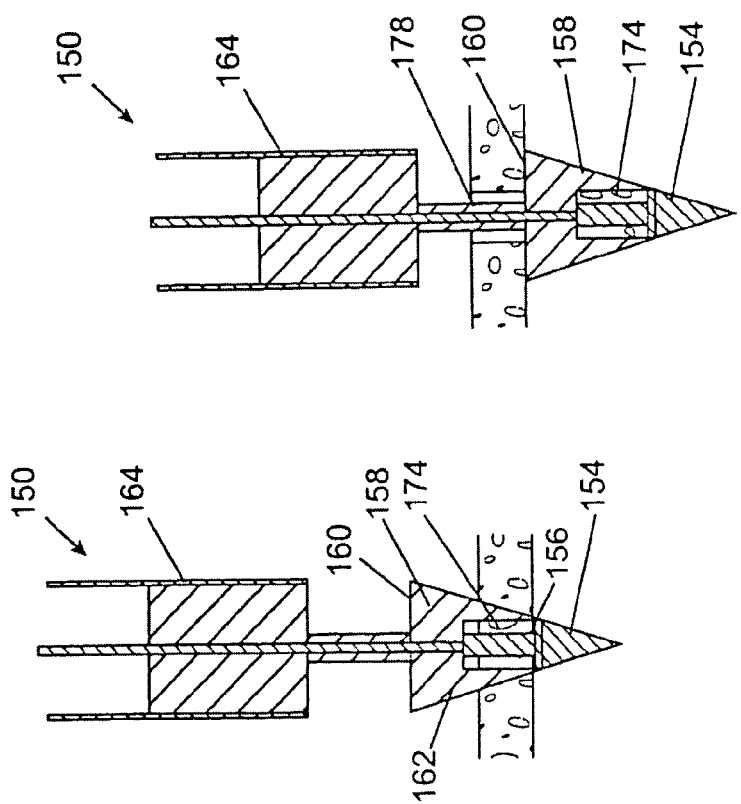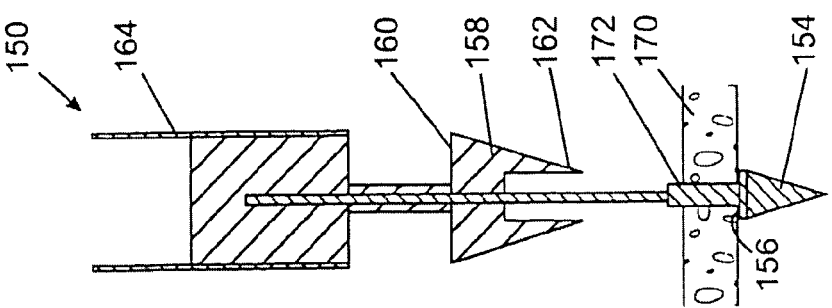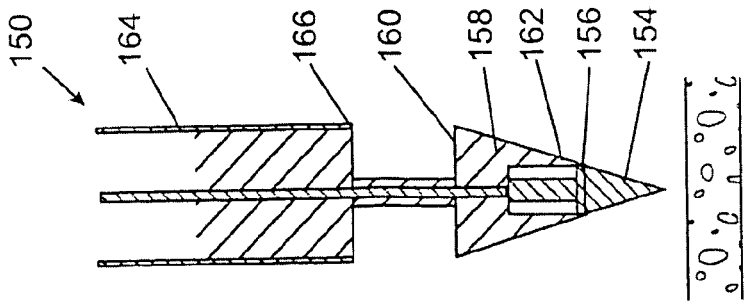

METHOD FOR CUTTING TISSUE

This application is a continuation of U.S. patent application Ser. No. 09/542,976, filed on Apr. 4, 2000 now U.S. Pat. No. 6,673,088; which in turn is a continuation-in-part of U.S. patent application Ser. No. 09/440,263, filed on Nov. 15, 1999 now U.S. Pat. No. 6,371,964; which in turn is a continuation-in-part of U.S. patent application Ser. No. 09/314,278 filed May 18, 1999 now U.S. Pat. No. 6,428,550; all of which are incorporated by reference in their entirety.

BACKGROUND OF THE INVENTION

1. Field of the Invention

The invention relates to a method of cutting tissue, and more particularly, the invention relates to forming an opening in a target blood vessel as part of a procedure for connecting a graft vessel to that target blood vessel.

2. Brief Description of the Related Art

Vascular anastomosis is a procedure by which two blood vessels within a patient are surgically joined together. Vascular anastomosis is performed during treatment of a variety of conditions including coronary artery disease, diseases of the great and peripheral vessels, organ transplantation, and trauma. In coronary artery disease (CAD) an occlusion or stenosis in a coronary artery interferes with blood flow to the heart muscle. Treatment of CAD involves the grafting of a vessel in the form of a prosthesis or harvested artery or vein to reroute blood flow around the occlusion and restore adequate blood flow to the heart muscle. This treatment is known as coronary artery bypass grafting (CABG).

In the conventional CABG, a large incision is made in the chest and the sternum is sawed in half to allow access to the heart. In addition, a heart lung machine is used to circulate the patients blood so that the heart can be stopped and the anastomosis can be performed. During this procedure, the aorta is clamped which can lead to trauma of the aortic tissue and/or dislodge plaque emboli, both of which increase the likelihood of neurological complications. In order to minimize the trauma to the patient induced by conventional CABG, less invasive techniques have been developed in which the surgery is performed through small incisions in the patients chest with the aid of visualizing scopes. Less invasive CABG can be performed on a beating or stopped heart and thus may avoid the need for cardiopulmonary bypass.

In both conventional and less invasive CABG procedures, the surgeon has to suture one end of the graft vessel to the coronary-artery and the other end of the graft vessel to a blood supplying vein or artery. The suturing-process is a time consuming and difficult procedure requiring a high level of surgical skill. In order to perform the suturing of the graft to the coronary artery and the blood supplying artery the surgeon must have relatively unobstructed access to the anastomosis site within the patient. In the less invasive surgical approaches, some of the major coronary arteries including the ascending aorta cannot be easily reached by the surgeon because of their location. This makes suturing either difficult or impossible for some coronary artery sites. In addition, some target vessels, such as heavily calcified coronary vessels, vessels having very small diameter, and previously bypassed vessels may make the suturing process difficult or impossible.

Accordingly, it would be desirable to provide a sutureless vascular anastomosis device which easily connects a graft vessel to a target vessel and can be deployed in limited space.

Deployment of a sutureless anastomosis device, such as those described in U.S. patent application Ser. No. 09/314,278, involves forming an opening in the target vessel and inserting the anastomosis device with a graft vessel attached into the opening. Accordingly, it would be desirable to provide a one piece tool which can perform both tissue punching and anastomosis device deployment. In order to provide a one piece device it would be desirable to provide a tissue punch which is advanced through a trocar and then is moved out of the trocar to allow deployment of the anastomosis device through the same trocar.

SUMMARY OF THE INVENTION

The present invention relates to a tissue punch for forming an opening in a target blood vessel for deploying an anastomosis device to connect a graft vessel to the target vessel.

In accordance with one aspect of the present invention, an apparatus for piercing a vessel, punching a hole in the vessel, removing punched tissue from the vessel, and introducing an object into the vessel through the punched hole is described. The apparatus includes a punch with a pointed piercing end for piercing a vessel to allow introduction of the punch into the vessel, a tubular element arranged coaxially with the punch through which the punch retracts to remove vessel tissue, and an introducer located coaxially around the tubular element. The introducer includes an area into which the punch and tubular element can be moved to allow introduction of an object into the punched hole-in the vessel through the introducer.

In accordance with another aspect of the present invention, a tissue punch includes a piercing element, a cutting edge, and a trocar receiving the piercing element. The piercing element has a pointed distal end, a tissue receiving space, and an anvil adjacent the tissue receiving space. The cutting edge is arranged to contact the anvil to cut a piece of tissue. The trocar has a side opening for removing the piercing element from the trocar after punching tissue.

In accordance with an additional aspect of the present invention, a method of punching a plug of tissue from the wall of a blood vessel includes the steps of penetrating the wall of the blood vessel with a piercing element to form an opening in the blood vessel, punching a plug of tissue around the opening in the blood vessel, and inserting a trocar into the punched hole in the blood vessel.

In accordance with a further aspect of the invention, a double tissue punch includes a piercing element having a pointed distal end and a first anvil surface; a first cutting element movable with respect to the piercing element, the first cutting element having a cutting edge arranged to contact the first anvil surface; and the first cutting element having a second anvil surface, a second cutting element movable with respect to the piercing element and the first cutting element, the second cutting element having a cutting edge arranged to contact the second anvil surface.

The present invention provides advantages of a tissue punch which is deployed through a trocar and is removed through a side wall of the trocar so that the trocar can subsequently be used for deployment of a medical device. The invention also provides the advantage of trapping a tissue plug which is cut by the tissue punch.

BRIEF DESCRIPTION OF THE DRAWINGS

The invention will now be described in greater detail with reference to the preferred embodiments illustrated in the accompanying drawings, in which like elements bear like reference numerals, and wherein:

FIG. 22 is a partially cut away perspective view of the tissue punch of FIG. 19 after tissue punching is completed;

FIG. 23 is a partially cut away perspective view of the tissue punch of FIG. 19 with the piercing element and tissue trap partially removed from the trocar;

FIG. 23A is an isolated perspective view of the piercing element and tissue trap of FIG. 23;

FIG. 24 is a perspective view of the tissue punch of FIG. 19 with the piercing element and tissue trap completely removed from the trocar; and FIGS. 25-30 are schematic side views of a double tissue punch showing a series of steps in a punching sequence with the double tissue punch.

DETAILED DESCRIPTION OF THE PREFERRED EMBODIMENTS

The tissue punch according to the present invention is used to create a hole in a wall of a target blood vessel for receiving an anastomosis device to connect a graft vessel to the target vessel. The tissue punch includes a piercing element for penetrating the target vessel wall, a cutter for cutting a plug of tissue, and a trocar which is inserted in the opening in the wall after punching has been completed. After punching is complete, the piercing element is removed from the trocar and the anastomosis device is then deployed through the open lumen of the trocar.

The tissue punch according to the present invention is particularly useful for use in coronary artery bypass grafting (CABG) in which a graft vessel is connected at opposite ends to the aorta and to a coronary artery. However, the target vessel which is punched with the tissue punch can be any vessel including but not limited to the aorta, coronary artery, and arteries leading to the arms or head. The graft vessel for connection to the target vessel can be an arterial graft, a venous graft, or a synthetic prosthesis, as required. The anastomosis procedure is preferably performed with minimally invasive procedures, without the stoppage of blood flow in the target vessel, and without the use of cardiopulmonary bypass. However, the anastomosis procedure may also be performed as a stopped heart and/or open chest procedure.

Preferably, the tissue punches according to the present invention are incorporated in a one piece tool which performs tissue punching and deployment of the anastomosis device. This one piece tool may be operated manually, such as by cams, or automatically, such as pneumatically.

Figure 1:
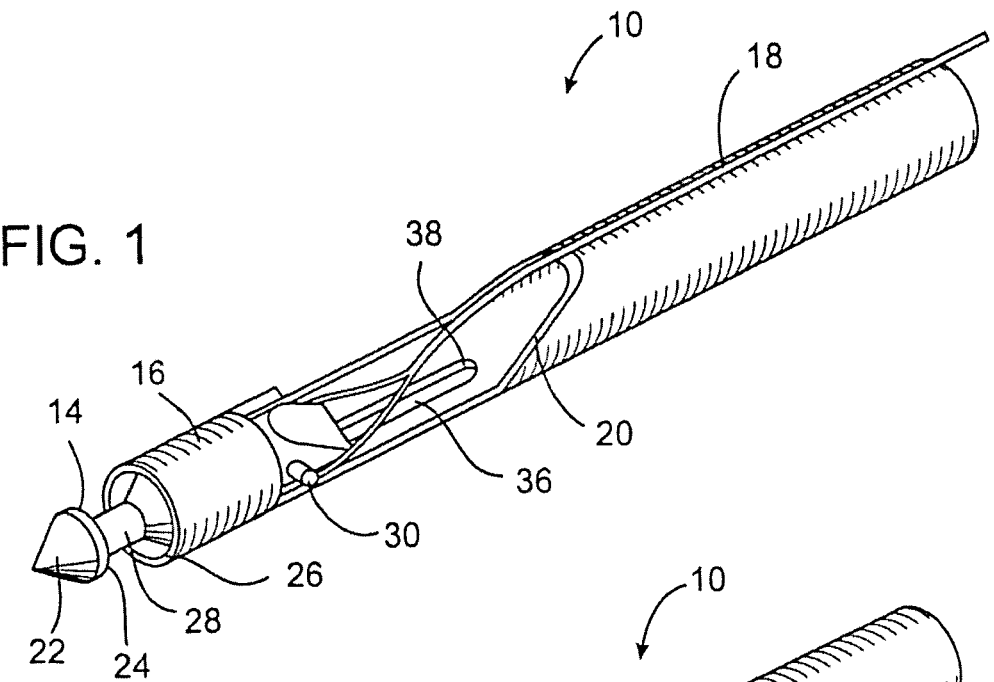
FIG. 1 is a perspective view of a tissue punch according to the present invention in a tissue penetrating position.

FIG. 1 is a perspective view of a tissue punch 10 according to the invention which includes a one-piece piercing element 14 positioned within an introducer sheath or trocar 16. The piercing element 14 can be advanced and retracted in the trocar 16 by an elongated member 18 such as a spring steel strap or cable which extends through an opening 20 in a side of the trocar. The piercing element 14 includes a pointed distal tip 22 for penetrating the target vessel wall and a narrow shaft portion 28 around which the tissue of the target vessel wall contracts after piercing. The distal tip 12 may be formed, for example, as a conical surface or by a plurality of ground surfaces extending to a point at the distal tip. An anvil surface 24 is located on the piercing element 14 between the distal tip 22 and the shaft 28. The anvil surface 24 acts with a cutting edge 26 of the trocar 16 to cut an annular plug of tissue.

In operation, the piercing element 14 is forcibly advanced to puncture the target vessel wall. After piercing, the tissue of the target vessel wall rests around the shaft portion 28 of the piercing element 14. The piercing element 14 is then pulled back inside the trocar 16 by the elongated member 18 to cut an annular plug of tissue by compressing the tissue between the anvil surface 24 of the piercing element and the cutting edge 26 of the trocar 16. The cut plug of tissue can be trapped in an annular space surrounding the shaft 28 and removed from the surgical site on the piercing element 14.

By using the tissue punch 10 to cut a plug of the target vessel wall tissue in this manner, there is less tendency for tearing. In particular, the punched opening in the vessel wall is less apt to tear than an incision or puncture. A puncture opening is particularly apt to tear when an anastomosis device is inserted into the opening or when the opening is expanded by expansion of the anastomosis device.

FIGS. 1-5 illustrate the steps of punching and then removing the piercing element 14 from the side opening of the trocar 16 to allow the anastomosis device to be deployed through the lumen of the trocar. In FIG. 1, the piercing element 14 is in an extended piercing position. In this position, the tissue punch is advanced into the target vessel wall. The tissue punch 10 is preferably advanced by spring actuated motion provided by a tool on which the tissue punch is mounted. Alternatively, the tissue punch may be advance manually.

Figure 2:
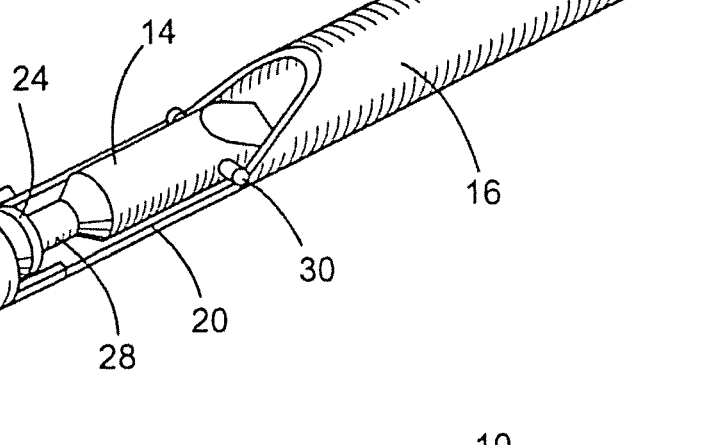
FIG. 2 is a perspective view of the tissue punch of FIG. 1 with the piercing element withdrawn inside the trocar.
Figure 3:
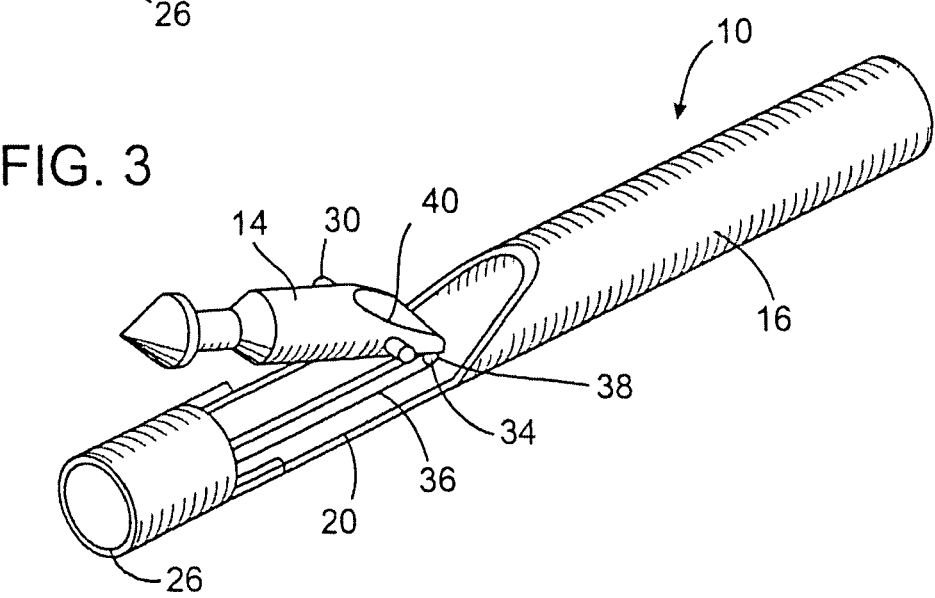
FIG. 3 is a perspective view of the tissue punch of FIG. 1 as the piercing element is pivoted out of the trocar.

As shown in FIG. 2, the piercing element 14 is withdrawn into the trocar 16 by pulling on the elongated member 18 (shown in FIG. 1). Once the distal tip 22 of the piercing element 14 clears the distal end of the opening 20, the piercing element is pivoted as it is retracted out of the opening 20 in the side of the trocar 16 as shown in FIGS. 3-5.

As shown in FIG. 1, the piercing element 14 includes two side pins 30 connected to the elongated member 18. The piercing element 14 is retracted by pulling on the elongated member 18 or other arrangement to accomplish punching of the tissue in the manner described above. During such retraction, a pin 34 on the underside of the piercing element 14 travels in a slot 36 in the trocar 16 until it reaches a stop 38 at the proximal end of the slot. When the pin 34 hits the stop 38, the piercing element 14 is caused to pivot about the stop as shown in FIG. 3.

Figure 4:
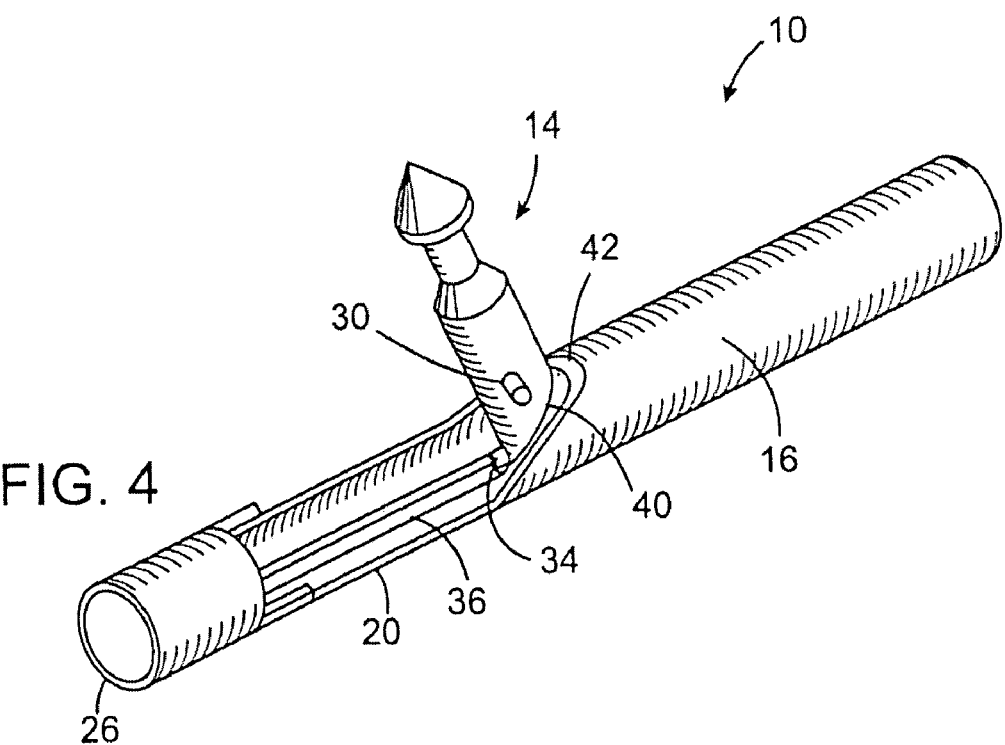
FIG. 4 is a perspective view of the tissue punch of FIG. 1 with the piercing element pivoted further.
Figure 5:
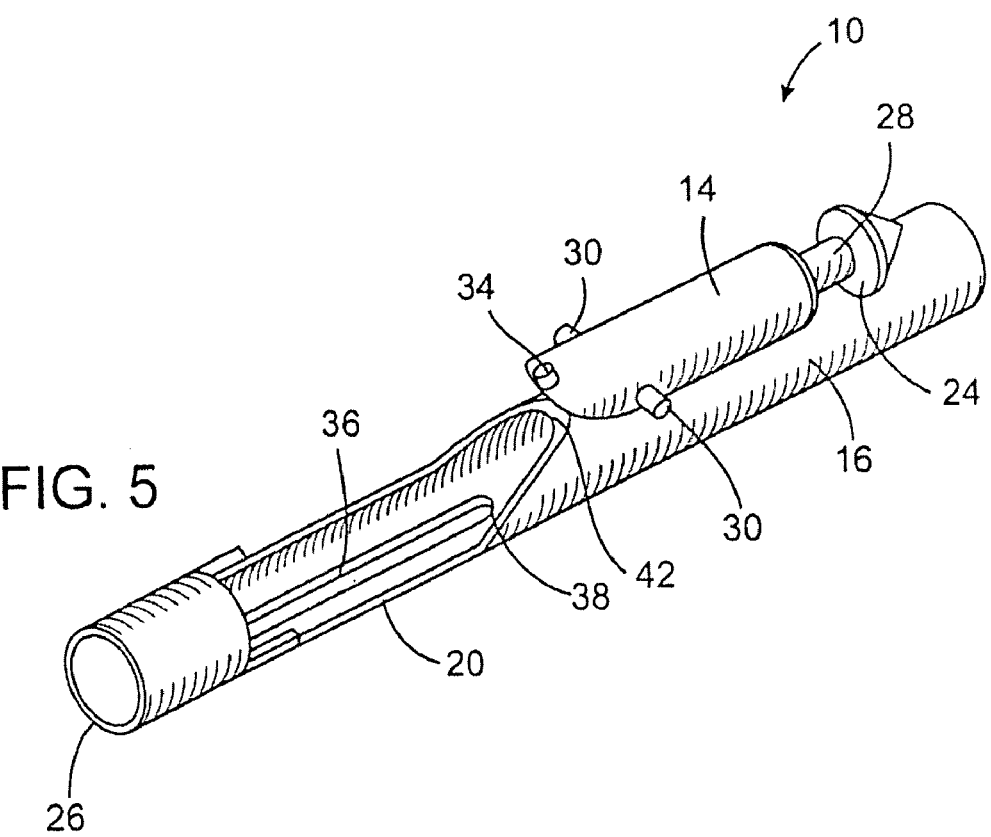
FIG. 5 is a perspective view of the tissue punch of FIG. 1 with the piercing element completely removed from the trocar.

Further retraction of the piercing element 14, as shown in FIG. 4, causes an inclined proximal surface 40 of the piercing element to contact an edge 42 of the trocar opening 20 such that the piercing element rotates out of the opening 20. As shown in FIG. 5, the piercing element continues to rotate to a storage position outside the trocar 16. When the piercing element is in the storage position, the inside of the trocar 16 can be used to maintain the opening in the blood vessel and for delivery of an anastomosis device to the incision in the target vessel.

FIGS. 6-24 illustrate alternative embodiments of tissue punches including, tissue traps for trapping and retaining the plug of tissue which is cut by the tissue punch. The trapping of tissue plug prevents possible complications which could occur if the plug of tissue is released in the surgical site.

Figure 6:
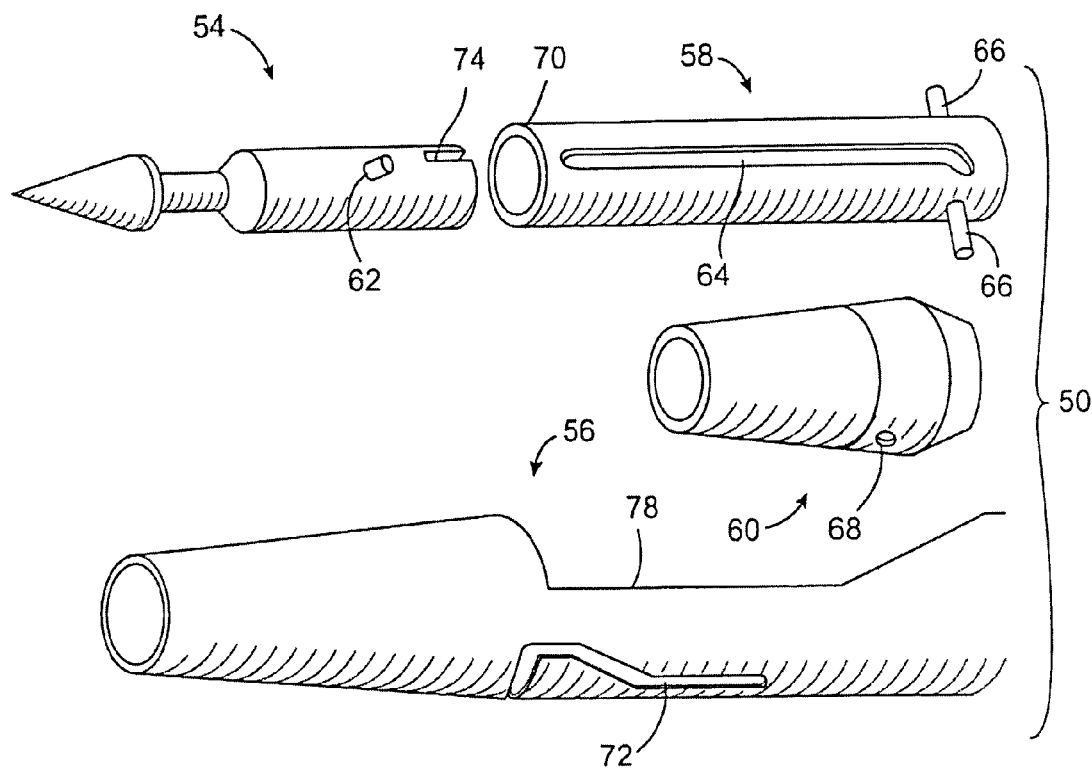
FIG. 6 is an exploded perspective view of a tissue punch having a cam release system.
Figure 7:
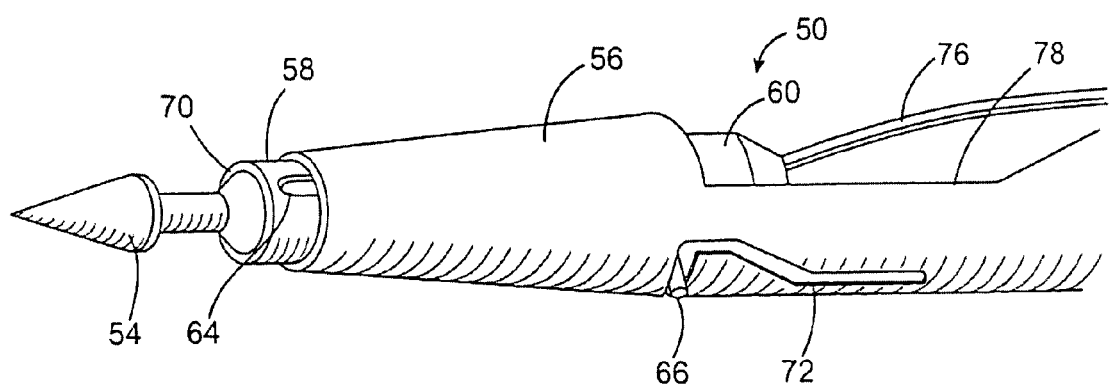
FIG. 7 is a perspective view of the tissue punch of FIG. 6 in an assembled, tissue penetrating position.

FIG. 6 illustrates a tissue punch 50 which includes a piercing element 54, a trocar 56, a tissue trap 58, and a collar 60. The tissue punch 50 is assembled as illustrated in FIG. 7 with the piercing element 54 positioned within the tubular tissue trap 58 with a pin 62 of the piercing element extending out through a slot 64 of the tissue trap. The tissue trap 58 includes two side pins 66 which extend through corresponding openings 68 in the collar 60. The side pins 66 also extend into cam slots 72 in the trocar 56. The piercing element 14 also includes a slot 74 at a proximal end which receives an elongated member 76 shown in FIG. 7. The elongated member 76 is preferably a spring steel strap which is used as a pull wire to pull the piercing element 54 into the tissue trap 58 and as a spring to move the piercing element and tissue trap out of the opening 78 in the side wall of the trocar 56.

Figure 8:
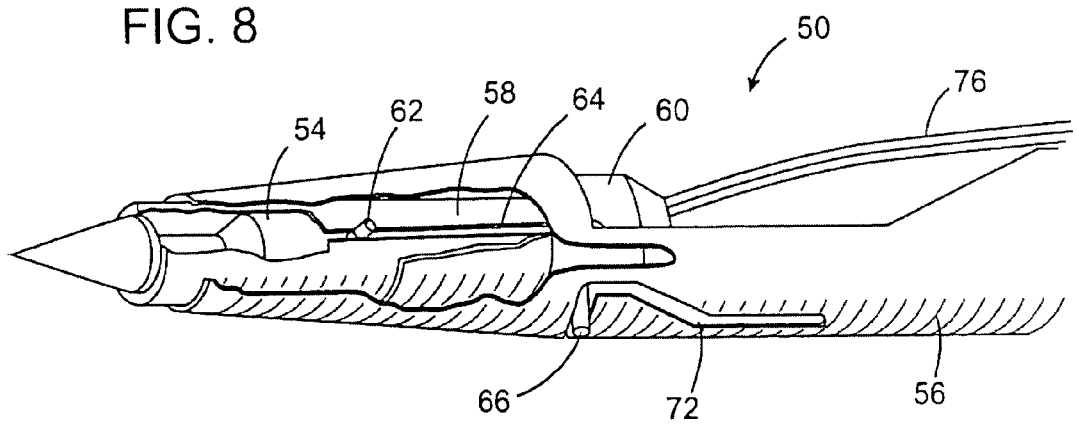
FIG. 8 is a partially cut away perspective view of the tissue punch of FIG. 6 in a tissue cutting position.

The punching procedure using the tissue punch 50 of FIGS. 6-12 will be described with respect to the sequence of steps shown in FIGS. 7-12. In the assembled position illustrated in FIG. 7, the piercing element 54 pierces the tissue of the blood vessel wall by automatic or manual advancement of the tissue punch. As shown in FIG. 8, after piercing the piercing element 54 is withdrawn inside the tissue trap 58 by pulling on the elongated member 76 to cut a plug of tissue with a cutting edge 70 of the tissue trap 58.

Figure 9:
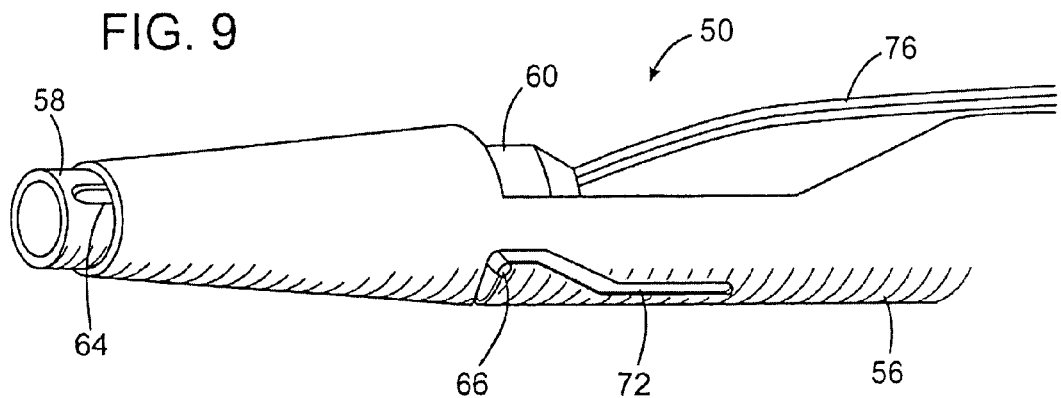
FIG. 9 is a perspective view of the tissue punch of FIG. 6 after tissue punching is completed.
Figure 10:
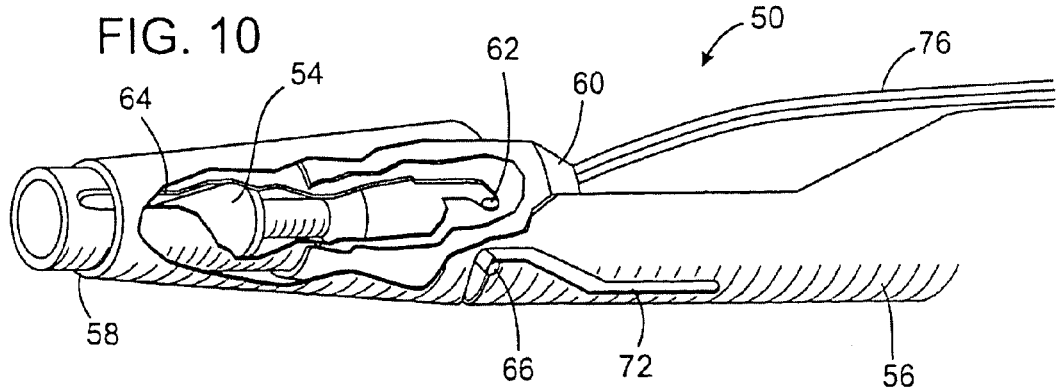
FIG. 10 is a partially cut away view of FIG. 9.
Figure 11:
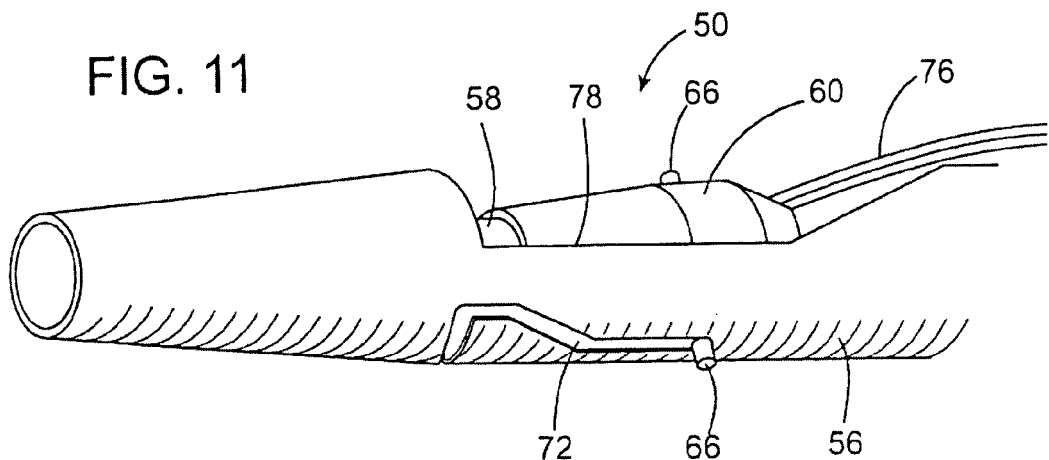
FIG. 11 is a perspective view of the tissue punch of FIG. 6 with the piercing element and tissue trap partially removed from the trocar.
Figure 12:
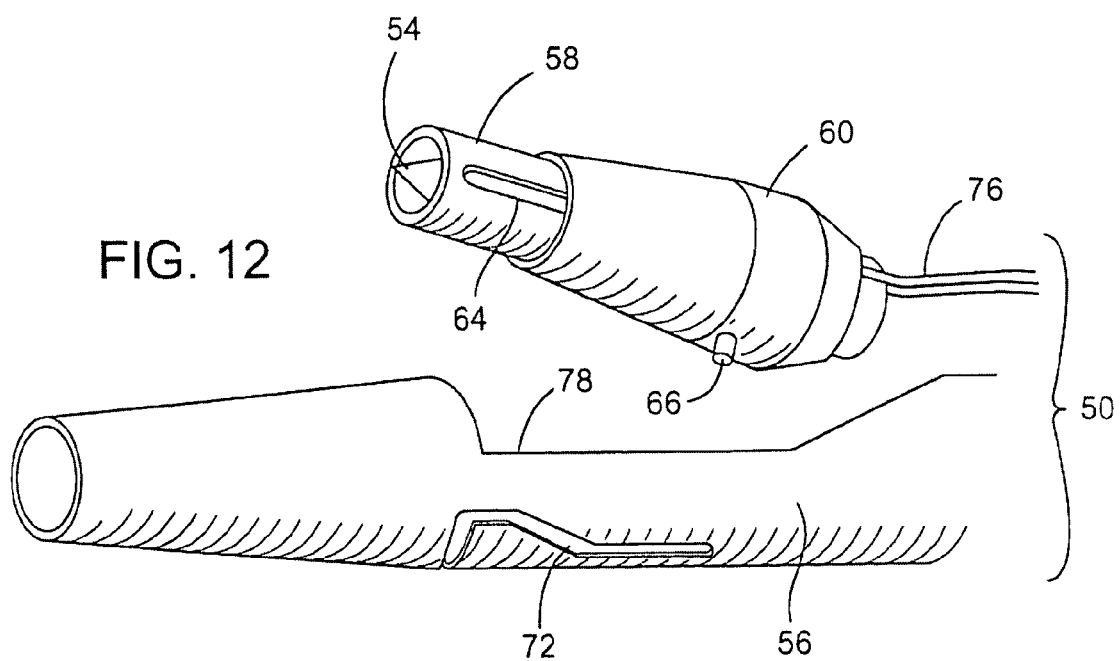
FIG. 12 is a perspective view of the tissue punch of FIG. 6 with the piercing element and tissue trap completely removed from the trocar.
Figure 13:
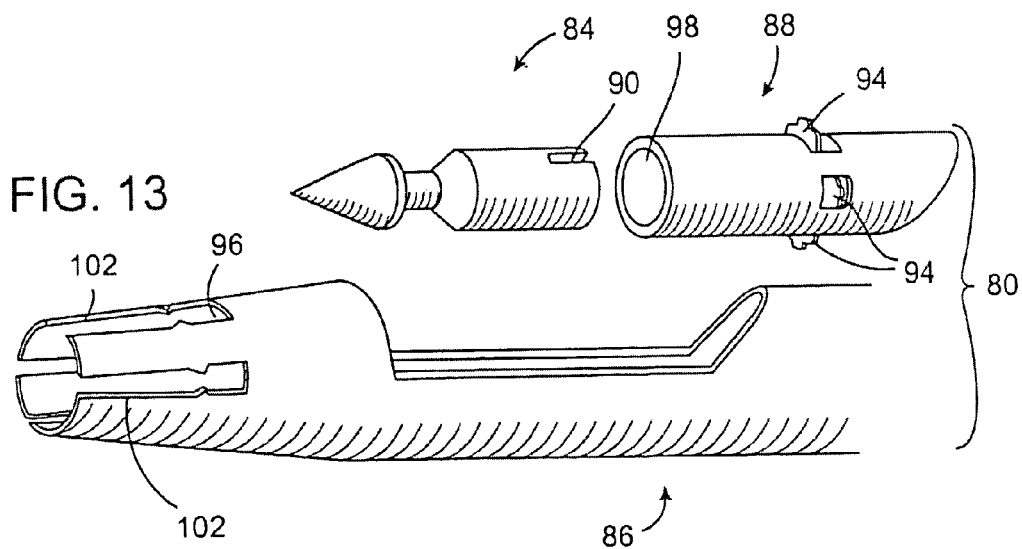
FIG. 13 is an exploded perspective view of a tissue punch having a bendable tab release system.

As shown in FIGS. 9 and 10, as the piercing element 54 is withdrawn, the pin 62 slides along the slot 64. When the pin 62 contacts the curved proximal end of the slot 64 the piercing element is prevented from rotating by the spring strap element 76 and the tissue trap is caused to rotate. When the tissue trap 58 rotates the side pins 66 rotate in the cam slot 72 unlocking the tissue trap and piercing element 54 from the trocar 56. As the tissue trap 56 is further withdrawn, as shown in FIG. 11, the tissue trap slides back into the opening 78 in the trocar 56. Finally, as shown in FIG. 12, the spring bias of the elongated spring member 76 causes the tissue trap 58 and piercing element 54 to be moved out of the trocar 56 to allow the lumen of the trocar to be used for deployment of a medical device, such as an anastomosis device.

The collar 60 of the tissue punch 50 is used as a spacer to hold the tissue trap 56 at a center of the trocar lumen. It should be understood that the collar 60 may be formed as a part of the tissue trap 58 or as a separate element.

FIGS. 13-18 illustrate an alternative embodiment of a tissue punch 80 having a bendable tab release system. As shown in the exploded view of FIG. 13, the tissue punch 80 includes a piercing element 84, a trocar 86, and a tissue trap 88. As in the embodiment of FIGS. 6-12, the piercing element 84 includes a proximal slot 90 for receiving an elongated member 94 which acts as a pull wire and spring. The tissue trap 88 includes a plurality of tabs 94 which are cut and folded out from the tube of the tissue trap. The trocar 86 includes a plurality of openings 96 for receiving the plurality of tabs 94. The plurality of openings 96 are also provided with slots 102 which extend to a distal end of the trocar 56.

Figure 14:
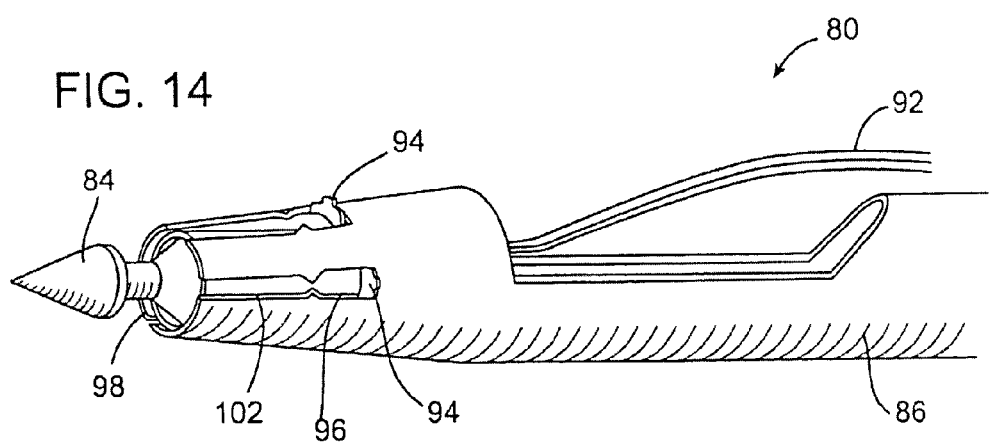
FIG. 14 is a perspective view of the tissue punch of FIG. 13 in an assembled tissue penetrating position.

As shown in FIG. 14, the tissue punch 80, in an assembled configuration prior to punching, axially has the tabs 94 positioned within the openings 96 to lock the tissue trap 88 in position axially with respect to the trocar 86. The tissue trap 88 is locked in place to allow cutting of the tissue with the cutting edge 98 of the tissue trap.

Figure 15:
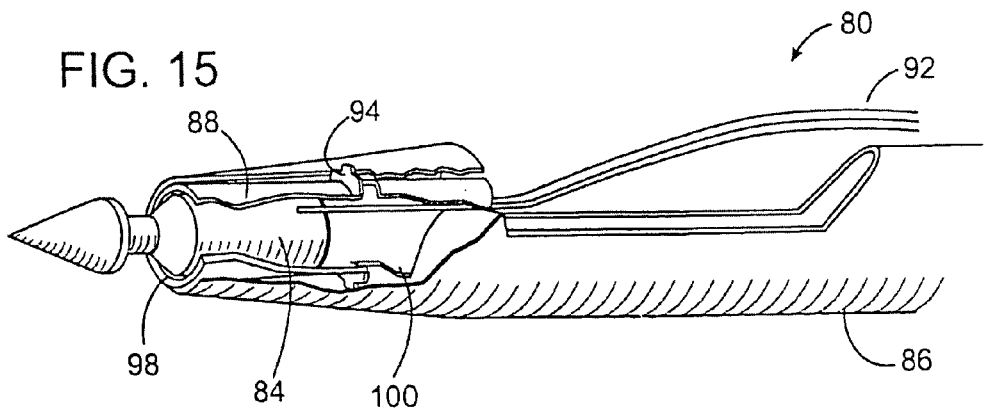
FIG. 15 is a partially cut away view of FIG. 14.
Figure 16:
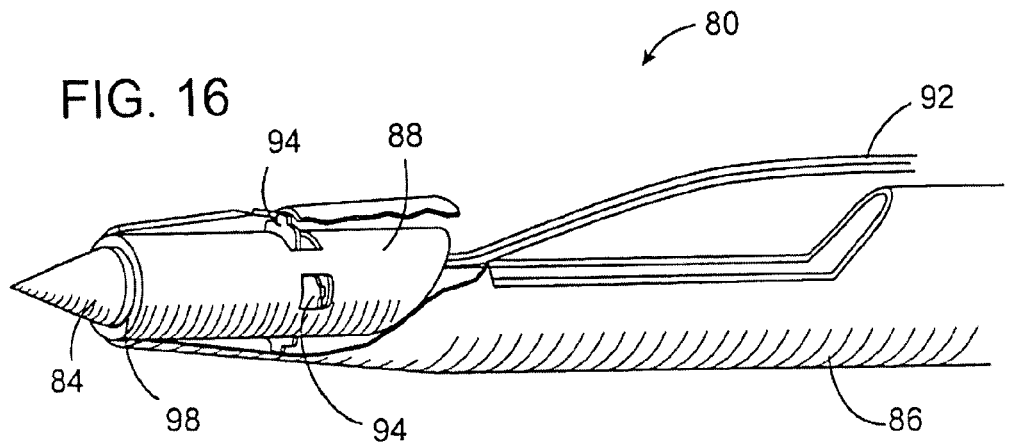
FIG. 16 is a partially cut away perspective view of the tissue punch of FIG. 13 after tissue cutting is completed.

The steps of operating the tissue punch 80 according to FIGS. 13-18 are illustrated in the sequence of steps shown in FIGS. 14-18. In FIGS. 14 and 15 the tissue punch is shown assembled for punching. The tissue punch is advanced into the tissue of a target vessel wall automatically or manually. Once the target vessel wall has been penetrated, the piercing element 84 is withdrawn by pulling on the elongated member 92 to cut a plug of tissue with the cutting edge 98. FIG. 16 illustrates the position of the piercing element 84 after punching is complete.

Figure 17:
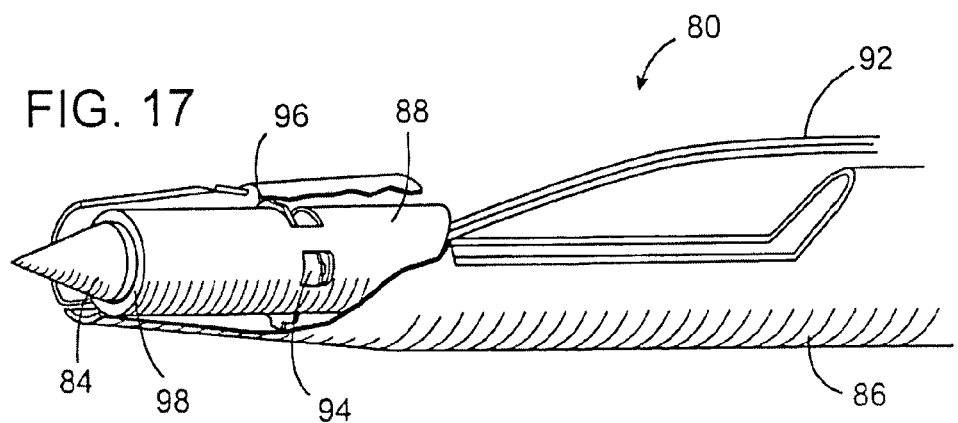
FIG. 17 is a partially cut away perspective view of the tissue punch of FIG. 13 with the piercing element and tissue trap partially removed from the trocar.
Figure 18:
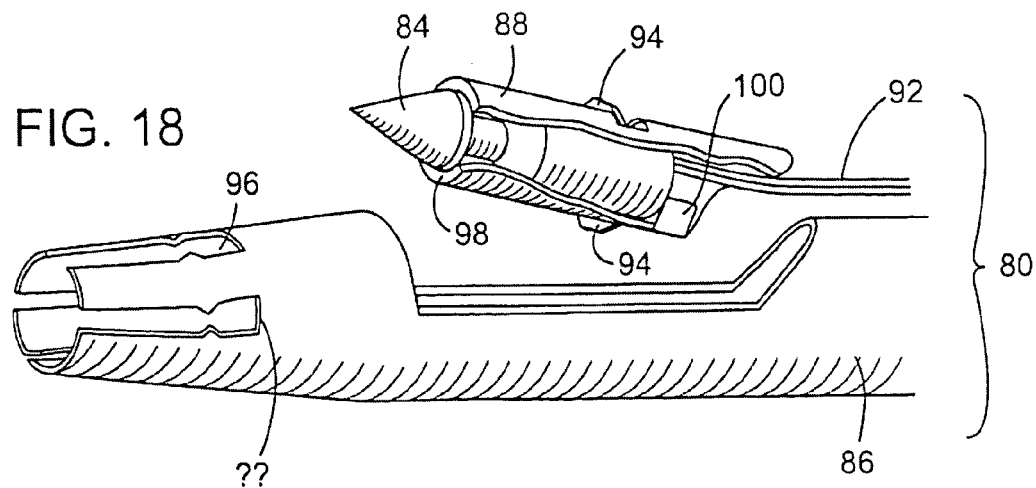
FIG. 18 is a partially cut away perspective view of the tissue punch of FIG. 13 with the piercing element and tissue trap completely removed from the trocar.
Figure 19:
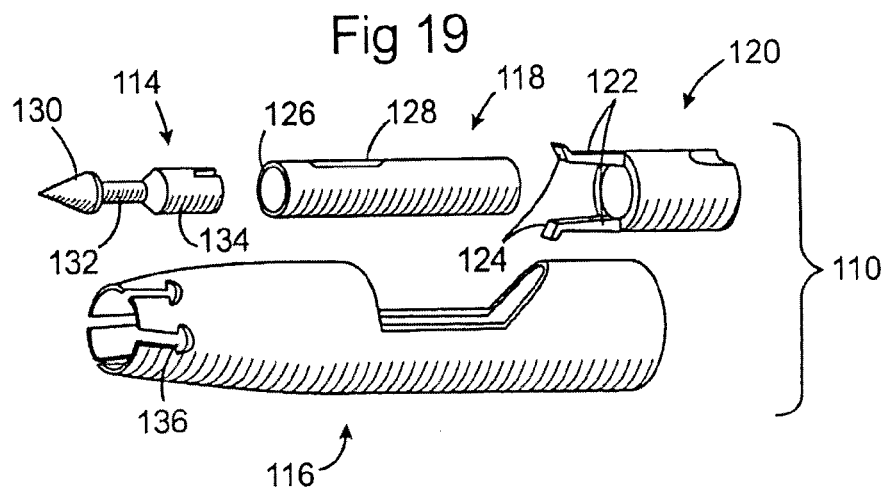
FIG. 19 is an exploded perspective view of a tissue punch having a snap release system.
Figure 20:
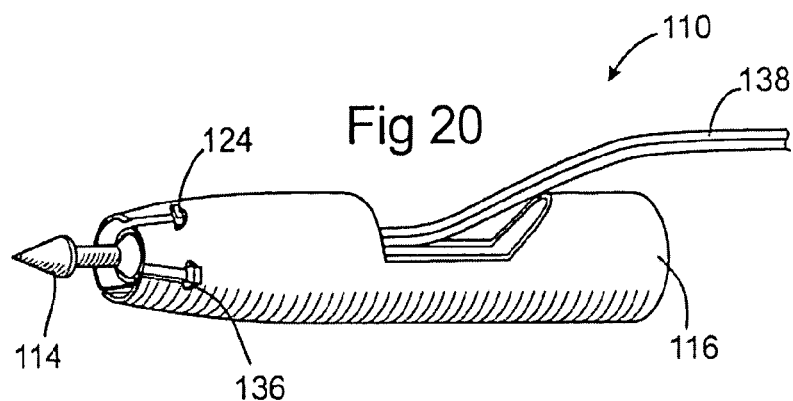
FIG. 20 is a perspective view of the tissue punch of FIG. 19 in an assembled tissue penetrating position.

As shown in FIG. 17, the piercing element 84 continues to be withdrawn until it abuts a stop member 100 inside the tissue trap 88. Continued withdrawal of the piercing element 84 pulls both the piercing element and the tissue trap 88 proximally and causes the tabs 94 to fold over allowing the tissue trap to be released from the trocar 86. As shown in FIG. 18, when the tissue trap 88 is released from the trocar 86, the spring force of the elongated member 92 moves the tissue trap and piercing element 84 out of the trocar.

Figure 21:
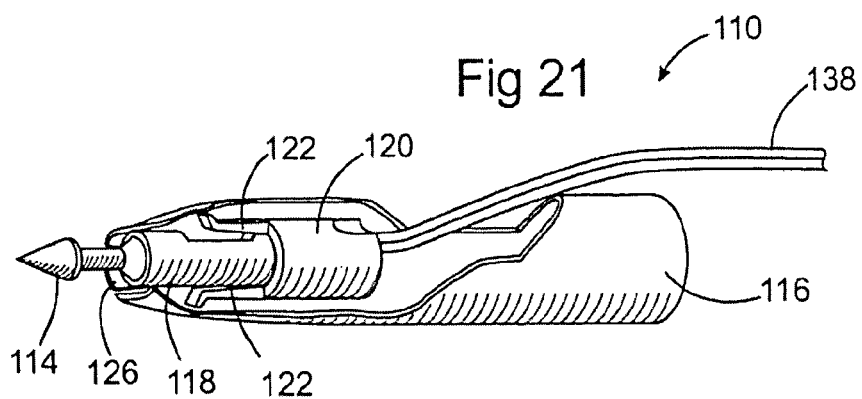
FIG. 21 is a partially cut away view of FIG. 20.
Figure 21A:
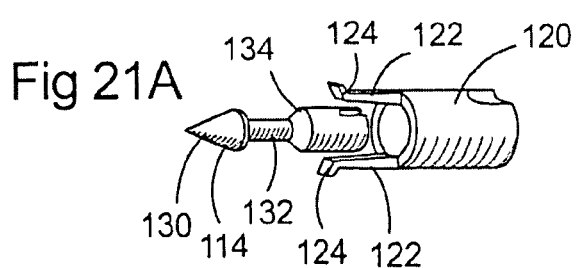
FIG. 21A is an isolated perspective view of the piercing element and tissue trap of FIG. 21.

FIGS. 19-24 illustrate a further embodiment of a tissue punch 110 having a snap release system. The tissue punch 110 includes a piercing element 114, a trocar 116, a tissue trap 118, and a collar 120. The collar 120 includes two legs 122 having tabs 124 at the ends. The collar 120 is fixed to the tissue trap 118. The tissue trap 118 has a cutting edge 126 and two slots 128 for accommodating the legs 122 and tabs 124 of the collar 120. The piercing element 114 has a tapered distal tip 130, a narrow shaft portion 132, and a larger shaft portion 134. In the assembled tissue penetrating position shown in FIGS. 20, 21, and 21A the tabs 124 are positioned adjacent the larger portion 134 of the shaft. The tabs 124 extend outward through openings 136 in the trocar 116 and lock the collar 120 and tissue trap 18 in position with respect to the trocar 166.

After punching, the piercing element 114, tissue trap 118, and collar 120 are removed as follows. As the piercing element 114 is withdrawn by the elongated member 138 as shown in 22, 23, and 23A, the tabs 124 of the collar 120 are positioned adjacent the narrow portion of the shaft 132. This allows the tabs 124 to flex inward releasing the tabs from the openings 136 in the trocar 116. Once the collar 120 is released from the trocar 116, the piercing element 114, the tissue trap 118 and the collar 120 move out of the trocar 116 by the spring action of the elongated member 138 and allow the trocar to be used for insertion of a medical device.

FIGS. 25-30 illustrate a sequence of tissue punching with a double punch system for forming an opening in the wall of a blood vessel. The double punch system 150 is used to make openings larger than those made by a single punch embodiment. For openings larger than about 3 mm a double punch is preferred since a piercing element with a largest diameter of greater than about 3 mm tends to cause excessive trauma to the tissue.

As shown in FIG. 25, the double punch system 150 includes a piercing element 154 having a first anvil 156, a spreading element 158 having a second anvil 160 and a first cutter 162, and a sleeve 164 having a second cutter 166. As shown in the sequence of FIGS. 26-30, the piercing element 154 is first inserted through the tissue 170 of a blood vessel wall until the tissue rests around a shaft 172 of the piercing element. The spreading element 158 is then moved downwards as shown in FIG. 27 to cut a first plug of tissue 174 with the first cutter 162. The first plug 174 is contained within an interior of the spreading element 158 which forms a tissue trap.

Figure 29:
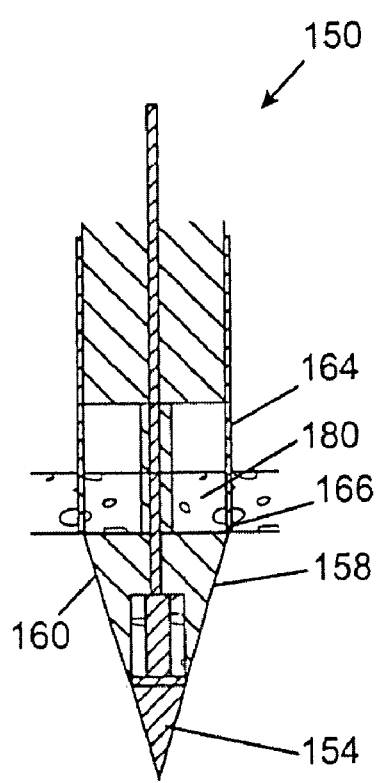

As shown in FIG. 28 the spreading element 158 is then advanced through the tissue 170 until the tissue rests around a shaft 178 of the spreading element. The sleeve 164 is then advanced, as shown in FIG. 29, to cut a second plug of tissue 180 with the second cutter 166. The second plug of tissue 180 is contained within the sleeve 164 which forms a tissue trap.

Figure 30:
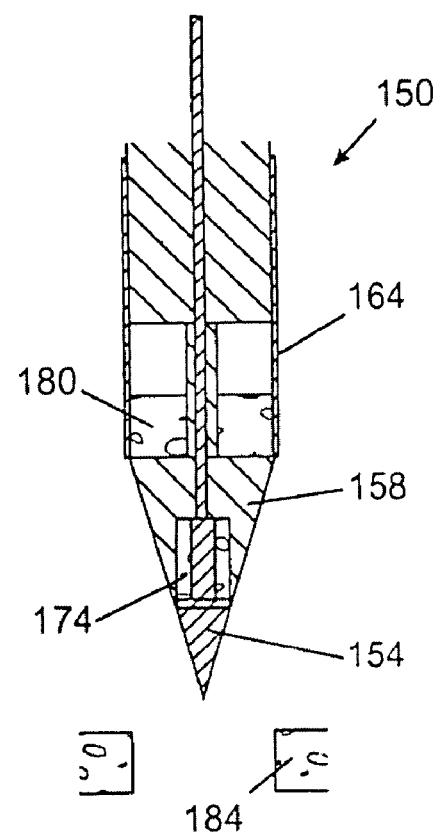

FIG. 30 illustrates the withdrawal of the double punch system 150 containing the two annular plugs 174, 180 of tissue and leaving a tissue opening 184.

It should be understood that the double punch system is illustrated as a system for forming holes which are larger than an approximately 3 mm hole which can be easily formed with a single punch system. The double punch system can form holes of up to about 8 mm in diameter without causing tissue trauma. In order to make holes of larger diameters additional spreading elements and cutting elements can be used to form a triple punch system or other multiple punch system.

While the invention has been described in detail with reference to the preferred embodiments thereof, it will be apparent to one skilled in the art that various changes and modifications can be made and equivalents employed, without departing from the present invention.

What is claimed is:

1. A method for making an opening in a vessel, comprising:
    piercing the wall of the vessel with a piercing element;
    retracting said piercing element at least partially into a tube having a lumen; and
    moving said piercing element away from the longitudinal centerline of said tube, after said retracting.

2. The method of claim 1, wherein said moving includes moving said piercing element through an opening in a side wall of said tube.

3. The method of claim 2, wherein a member is attached to said piercing element and extends through said opening; and wherein said moving includes applying force to said member.

4. The method of claim 2, wherein said moving includes separating said piercing element from said tube.

5. The method of claim 2, wherein said moving comprises pivoting said piercing element at least partially through said opening.

6. The method of claim 2, further comprising storing said piercing element adjacent to said tube.

7. The method of claim 1, wherein said retracting cuts a tissue plug from the wall of the vessel.

8. The method of claim 7, further comprising retaining the tissue plug with said piercing element.

9. A method for making an opening in the wall of a hollow tissue structure, comprising:
    piercing the wall of the hollow tissue structure, at a location in the wall through which fluid previously had been substantially prevented from escaping, with a piercing element to create an opening therethrough;
    retracting the piercing element toward an opening in a body to cut a tissue plug from the wall of the hollow tissue structure;
    capturing the tissue plug with said piercing element; and
    moving said piercing element away from the longitudinal centerline of said body after said capturing.

10. The method of claim 9, wherein said body is a tube.

11. The method of claim 9, wherein said opening in said body has a cutting edge defined thereon.

12. The method of claim 9, wherein said piercing element includes a pointed tip and an anvil surface proximal to said pointed tip, and wherein said retracting moves said anvil surface toward said opening in said body to cut the tissue plug.

13. The method of claim 9, wherein said piercing is performed by urging said piercing element distally with spring force.

14. The method of claim 9, wherein said piercing is performed by manually advancing said piercing element in the distal direction.

15. The method of claim 9, wherein said body includes a side opening defined therein; and wherein said moving is through said side opening.

* * * * *